United States Patent [19]

Hutson, Jr.

[11] 4,026,961
[45] May 31, 1977

[54] ISOPARAFFIN HF ALKYLATION WITH LOW-BOILING ALKYL FLUORIDE-CONTAINING FRACTION

[75] Inventor: Thomas Hutson, Jr., Bartlesville, Okla.

[73] Assignee: Phillips Petroleum Company, Bartlesville, Okla.

[22] Filed: Sept. 15, 1975

[21] Appl. No.: 613,763

[52] U.S. Cl. .......................................... 260/683.49
[51] Int. Cl.² .......................................... C07C 3/54
[58] Field of Search ............... 260/683.49, 683.48, 260/677 XA, 648 F, 653.6, 652 P

[56] References Cited

UNITED STATES PATENTS

| 2,333,648 | 11/1943 | Grosse et al. | 260/677 XA |
| 2,347,317 | 4/1944 | Gibson | 260/683.49 |
| 2,387,162 | 10/1945 | Matuszak | 260/683.48 |
| 2,434,000 | 1/1948 | Matuszak | 260/683.49 |
| 2,456,435 | 12/1948 | Matuszak | 260/653.6 |
| 2,832,812 | 4/1958 | Belden | 260/653.6 |
| 2,917,559 | 12/1959 | Sweeney | 260/653.6 |
| 3,240,834 | 3/1966 | Kruse et al. | 260/677 XA |
| 3,372,207 | 3/1958 | Hutson, Jr. | 260/652 P |
| 3,872,181 | 3/1975 | Chapman | 260/683.49 |

Primary Examiner—George Crasanakis

[57] ABSTRACT

High quality motor fuel alkylate is produced in a combination process comprising hydrofluorination of an olefin-containing hydrocarbon stream with HF to produce alkyl fluorides, separation of the produced alkyl fluorides into a low boiling fraction and a high boiling fraction, and subjecting the low boiling fraction to HF alkylation with an isoparaffin. In another embodiment, the high boiling alkyl fluoride polymer fraction is dehydrofluorinated and the produced lower boiling olefins and HF therefrom are recycled to the hydrofluorination step.

10 Claims, 1 Drawing Figure

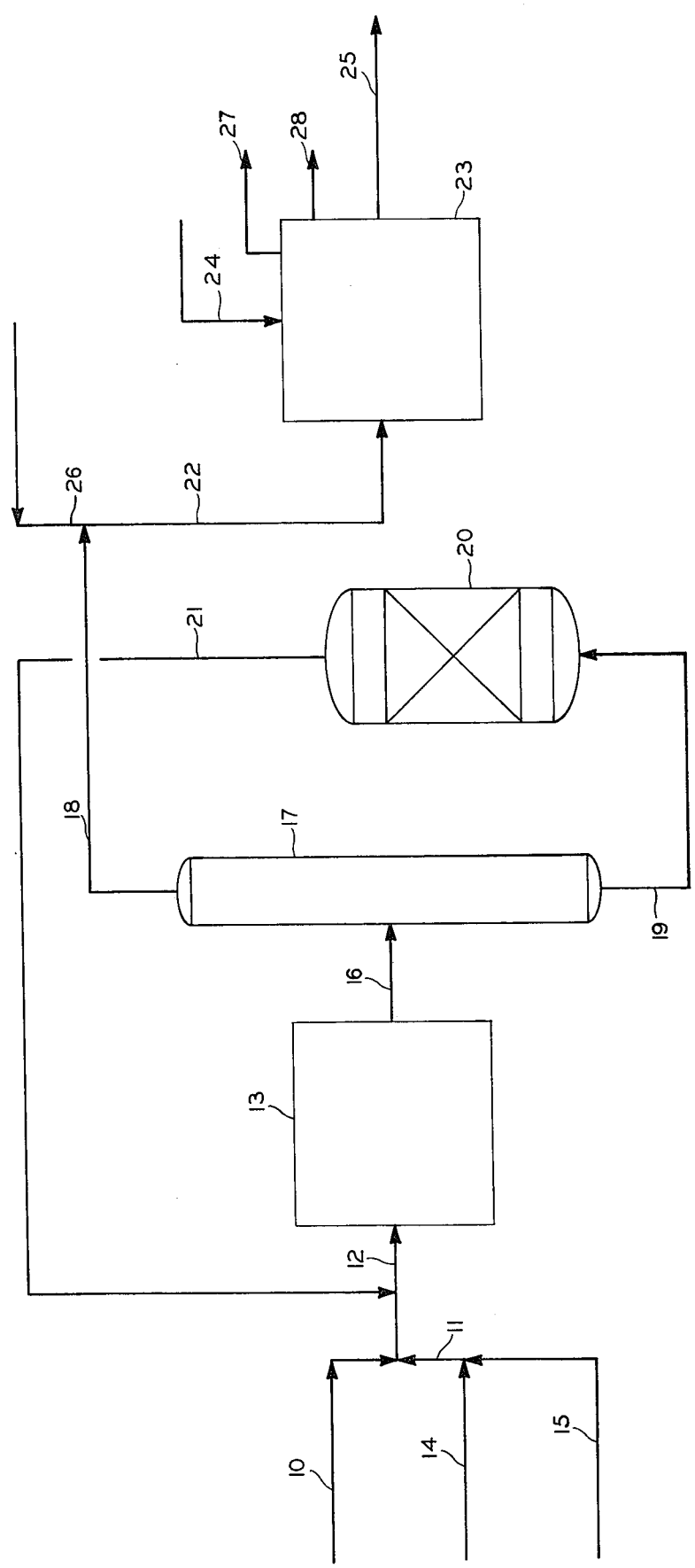

ISOPARAFFIN HF ALKYLATION WITH LOW-BOILING ALKYL FLUORIDE-CONTAINING FRACTION

This invention relates to an improved process for the production of high quality alkylate. In accordance with another aspect, the invention relates to an improved process comprising a combination of steps of hydrofluorinating an olefin-containing hydrocarbon stream to produce alkyl fluorides, separation of the alkyl fluorides into a high boiling and a low boiling fraction, and alkylation of the low boiling fraction thus separated. In accordance with a further aspect, this invention relates to a combination process comprising hydrofluorination, distillation, dehydrofluorination, and alkylation. In accordance with a further aspect, this invention relates to a combination hydrofluorination-alkylation process comprising hydrofluorinating an olefin with HF to produce alkyl fluorides, separation of the high boiling alkyl fluoride polymers from the produced alkyl fluorides, and subjecting the low boiling range alkyl fluorides to HF alkylation, thereby removing from the process undesirable high boiling alkyl fluorides which produce low octane alkylate.

It is known in the art to hydrofluorinate olefinic hydrocarbons with HF to produce alkyl fluorides and then subjecting the alkyl fluorides to alkylation with an isoparaffin in the presence of HF. It is also known that alkyl fluorides can be dehydrofluorinated to produce olefins and HF. One problem encountered in the hydrofluorination of olefins followed by alkylation of the produced alkyl fluorides is that during hydrofluorination of an olefin with HF there are produced high boiling alkyl fluorides which when used to HF alkylate an isoparaffin produce a low octane alkylate. The present invention overcomes this problem by removing the high boiling alkyl fluorides from the produced alkyl fluorides, sending only the desired boiling range alkyl fluorides to HF alkylation. In addition, the high boiling alkyl fluorides are recovered and converted back by dehydrofluorination into olefins and HF which can be charged to the hydrofluorination step.

Accordingly, an object of this invention is to provide an improved process for alkylation.

Another object of this invention is to provide an improved combination process of hydrofluorination and alkylation to produce high quality alkylate.

A further object of this invention is to provide a process for removing undesirable alkylation feed components which have a tendency to reduce alkylate quality.

A further object of this invention is to provide an economical and practical process comprising the combination of hydrofluorination, dehydrofluorination, and alkylation.

Other objects, aspects, and the several advantages of the invention will be apparent to those skilled in the art upon reading the specification and the appended claims.

In accordance with the invention, an improved process for production of high quality motor fuel alkylate is provided which comprises hydrofluorinating an olefin-containing hydrocarbon stream with HF to produce alkyl fluorides, separating the alkyl fluorides into a high boiling fraction and a low boiling fraction, and subjecting the low boiling fraction to HF alkylation with an isoparaffin to produce the high quality motor fuel alkylate.

In accordance with another embodiment, high quality motor fuel alkylate is produced by a combination of steps comprising hydrofluorinating an olefin-containing hydrocarbon stream with HF to produce alkyl fluorides, distilling the alkyl fluorides thus produced into a low boiling and a high boiling fraction, dehydrofluorinating the high boiling fraction to produce olefins and HF which can be recycled to the hydrofluorination step as part of the feed, and subjecting the low boiling fraction to HF alkylation with an isoparaffin to produce a high quality motor fuel alkylate.

The conditions for carrying out the hydrofluorination, dehydrofluorination, and alkylation steps of the present invention are well known in the art. The present invention is directed to a novel combination of steps known in the art, the individual steps being known in the art but being arranged according to the invention in such a manner as to obviate problems encountered in the prior art and produce a high quality motor fuel alkylate.

In the first step of the present process, i.e., the hydrofluorination, a suitable olefin-containing hydrocarbon stream feed that can be employed include generally $C_3$–$C_6$ monoolefins. The preferred olefinic reactants are those used in conventional isoparaffin-olefin alkylation processes including propylene, 1-butene, 2-butene, isobutylene, amylenes, and the like. It is presently preferred to use 1-butene for hydrofluorination and subsequently for reaction with an isoparaffin in the alkylation zone. It is also within the scope of the invention to use a mixed hydrocarbon stream comprising olefinic and isoparaffinic hydrocarbon as feed to the hydrofluorination zone. The mol ratio of isoparaffin to olefin will ordinarily range from 0.5/1 to 10/1. The hydrofluorination temperature is sufficient to hydrofluorinate the olefinic hydrocarbons present in the feed to produce alkyl fluoride and generally will be in the range of −40° to 40° F. The pressure is ordinarily sufficient to maintain liquid phase conditions and can range from, say, about 50 to about 100 psig. The period of time for carrying out the reaction can range from 0.1 to, say, 30 minutes, or more. The volume ratio of HF to hydrocarbon can be in the range of about 0.01 to 0.5.

The alkyl fluorides produced in the first stage according to the invention are subjected to distillation to separate overhead the low boiling alkyl fluoride fraction comprising alkyl fluorides and hydrocarbons boiling in the range of about 10° F. to about 140° F. and a high boiling bottoms fraction comprising alkyl fluorides and hydrocarbons boiling above about 140° F. The distillation zone is operated under conditions such that the low boiling fraction and the high boiling fraction having the boiling ranges set forth are separated and passed to further treatment as set forth below.

The high boiling fraction comprising alkyl fluorides and hydrocarbons boiling generally above about 140° F. is subjected to dehydrofluorination under conditions which will convert the alkyl fluorides to olefins and HF. The process can be carried out in the presence of suitable catalysts such as metals, for example, aluminum, iron, lead, etc., metal oxides such as alumina, aluminum fluoride, calcium fluoride, and the like. These materials can be combined with suitable carriers. The conditions of temperature and pressure for carrying out the dehydrofluorination reaction are sufficient to convert the high boiling alkyl fluorides to olefins and HF and ordinarily will include a temperature in the range of 250° F. to 1,000° F. and a pressure of 100 to 1,000 psig, and contact time of about 0.25 to 1 minute.

The low boiling fraction comprising alkyl fluorides and hydrocarbons boiling in the range of about 10° F. to about 140° F. is passed to conventional HF alkylation zone wherein the alkyl fluorides are contacted with isoparaffin under conditions which produce alkylate. The conditions for carrying out the alkylation are well known, but ordinarily the temperature will be in the range of about −40° to 125° F. and sufficient pressure to maintain liquid phase conditions, for example, pressures of 50 to 200 psig. The isoparaffin to alkyl fluoride mol ratio will ordinarily range from 2/1 to 50/1 and the HF to hydrocarbon volume ratio will be in the range of about 1/1 to 20/1, and contact time of about 10 to 600 seconds. A better understanding of the invention will be obtained upon reference to the accompanying drawing which diagrammatically illustrates the preferred embodiment of the invention. Referring now to the drawing, HF introduced by line 10 is combined with a mixed olefin-isoparaffin stream in line 11 and the mixed stream plus HF is passed by way of line 12 to hydrofluorination zone 13. The mixed feedstream in line 11 comprises olefinic hydrocarbons introduced by line 14 and isoparaffinic hydrocarbons introduced by way of line 15.

The olefinic-containing hydrocarbon feedstream is subjected to hydrofluorination conditions in the presence of HF in zone 13 to produce an effluent 16 comprising alkyl fluorides and hydrocarbons including olefin as well as paraffins and isoparaffins. The alkyl fluoride-containing stream 16 is passed to distillation zone 17 wherein the feedstream is subjected to distillation conditions whereby a low boiling fraction comprising alkyl fluorides and hydrocarbons is removed overhead by line 18 and a high boiling fraction comprising alkyl fluorides and hydrocarbons is removed as bottoms by way of line 19. The low boiling overhead fraction will ordinarily have a boiling range of about 10° F. to about 140° F. and the high boiling bottoms fraction will boil above about 140° F.

The high boiling alkyl fluoride-containing fraction in line 19 is passed to dehydrofluorination zone 20 wherein the fraction is subjected to dehydrofluorination conditions such that the alkyl fluorides are converted to olefins and HF. The produced olefins and HF from zone 20 are recovered by way of line 21 and recycled as part of the feed to hydrofluorination zone 13 by being introduced into feed line 12. The dehydrofluorination zone reaction can be carried out in the presence of suitable contact materials.

The low boiling alkyl fluoride-containing fraction in line 18 is combined with additional isoparaffin as needed in line 26, and the mixed stream is passed by way of line 22 to alkylation zone 23. Also introduced into alkylation zone 23 is HF by way of line 24. Within alkylation zone 23 the alkyl fluorides and isoparaffin feed are subjected to alkylation conditions such that alkylate is produced which is removed by way of line 25 for further treatment as desired. Propane and normal butane yield are removed via conduits 27 and 28, respectively.

As can be seen from the above description, the high boiling alkyl fluorides which produce low octane alkylate are removed according to the invention from the system and converted to desirable hydrofluorination feedstock by dehydrofluorination of the alkyl fluorides, and the low boiling alkyl fluorides which increase alkylate quality are used as feed to the alkylation zone.

The following calculated example will better illustrate the invention. In this example, butene-1, isobutane, and HF are contacted under hydrofluorination conditions, the effluent is distilled into two fractions, one being sent as at least part of the feed to alkylation and the other being subjected to dehydrofluorination and recycle in accordance with the embodiments described in connection with the drawing. The reactants and conditions used the various steps of the process as are set forth below.

| | | |
|---|---|---|
| Hydrofluorination 13: | | |
| Temperature, ° F. | 20 | (−6.7° C.) |
| Pressure, psig | 65 | (445 KPa) |
| Contact time, minutes | 0.5 | |
| Isoparaffin/Olefin, mol ratio | 2.45 | |
| HF/Hydrocarbon vol. ratio | 0.048 | |
| HF Charged (stream 10), grams/hour | 2,200 | |
| Total Butene-1 Charged (stream 14), grams/hour | 7,567 | |
| Isobutane Charged (stream 15), grams/hour | 20,167 | |
| Recycle Butene-1 (stream 21), grams/hour | 791 | |
| Recycle HF (stream 21), grams/hour | 141 | |
| Butene-1 Conversion = 81.4 Percent | | |
| Fractionation 17: | | |
| Top: | | |
| Temperature, ° F. | 125 | (51.7° C.) |
| Pressure, psig | 52 | (355 KPa) |
| Bottom: | | |
| Temperature, ° F. | 430 | (221.1° C.) |
| Pressure, psig | 60 | (410 KPa) |
| Overhead Yield (stream 18), grams/hour | 26,802 | |
| Composition, Weight Percent: | | |
| HF, grams/hour | — | |
| Propane | Trace | |
| Isobutane | 64.15 | |
| N-Butane | 3.00 | |
| Butene-1 | 3.74 | |
| Butene-2 | 0.43 | |
| 2-Fluorobutane | 28.65 | |
| Isopentane | 0.03 | |
| Bottoms (stream 19) yield, grams/hour | 932 | |
| Composition, Weight Percent: | | |
| HF | 0 | |
| Isopentane | Trace | |
| 2-Fluorobutane | 0.3 | |
| Residue | 99.7 | |
| Dehydrofluorination 20: | | |
| Contact material | Activated carbon | |
| Temperature, ° F. | 500 | (260° C.) |
| Pressure, psig | 500 | (3450 KPa) |
| Contact Time, min. | .4 | |
| Product: | | |
| HF, grams/hour | 141 | |
| Butene-1, grams/hour | 791 | |
| HF Alkylation 23: | | |
| Temperature, ° F. | 42 | (5.6° C.) |
| Pressure, psig | 150 | (1030 KPa) |
| Contact Time, seconds | 30 | |
| iC$_4$/Alkyl Fluoride mol ratio | 5.5 | |
| HF/Hydrocarbon vol. ratio | 10 | |
| Alkylate Product 25: (375° F. End Point) | | |
| Yield, grams/hour | 13,965 | |
| RON, clear | 94.9 | |
| MON, clear | 93.7 | |

When the total alkyl fluoride 16 is charged to the HF alkylation (same conditions as in the above example) there is produced 12,500 grams per hour of alkylate, RON clear of 94.0 and MON clear of 93.0. RON is Research Octane Number. MON is Motor Octane Number.

I claim:

1. An improved process fro the production of high quality motor fuel alkylate which comprises the steps of:
   a. hydrofluorinating an olefin-containing hydrocarbon stream with HF under hydrofluorination conditions which produce alkyl fluorides,
   b. distilling the produced alkyl fluorides obtained in step (a) under conditions to separate a low-boiling alkyl fluoride-containing fraction overhead and a high-boiling alkyl fluoride-containing fraction as bottoms,
   c. dehydrofluorinating said high-boiling alkyl fluoride-containing fraction obtained in (b) under dehydrofluorination conditions which produce olefins and HF, and
   d. passing said low-boiling alkyl fluoride-containing fraction obtained in (b) to an alkylation zone and therein contacting the same with isoparaffin and HF under alkylation conditions to produce said high quality alkylate.

2. A process according to claim 1 wherein the olefins and HF produced in step (c) are recycled to step (a) as part of the feed to the hydrofluorination.

3. A process according to calim 1 wherein said low boiling alkyl fluoride-containing fraction comprises alkyl fluorides and hydrocarbons boiling in the range of about 10° to about 140° F. and said high boiling alkyl fluoride-containing fraction comprises alkyl fluorides and hydrocarbons boiling above about 140° F.

4. A process according to claim 1 wherein said olefin-containing hydrocarbon stream comprises a mixture of olefinic and isoparaffinic hydrocarbons in a mol ratio of isoparaffin to olefin of about 0.5/1 to 10/1.

5. A process according to claim 1 wherein said olefin-containing stream comprises a mixture of olefinic and isoparaffinic hydrocarbons in a mol ratio of isoparaffin to olefins of about 0.5/1 to 10/1 and further wherein said low boiling alkyl fluoride-containing fraction comprises alkyl fluorides and hydrocarbons boiling in the range of about 10° to about 140° F. and said high boiling alkyl fluoride-containing fraction comprises alkyl fluorides and hydrocarbons boiling above about 140° F.

6. A process according to claim 5 wherein said olefin-containing stream comprises a mixture of $C_4$ olefinic and isoparaffinic hydrocarbons.

7. In a process for the alkylation of isoparaffinic hydrocarbons wherein olefins are reacted with HF under hydrofluorination conditions in a first stage and alkyl fluorides are reacted with isoparaffins in a second stage under alkylation conditions and in the presence of HF, the improvement which comprises the steps of
   a. distilling the alkyl fluorides produced in said first stage under conditions to separate a low boiling fraction comprising alkyl fluorides and hydrocarbons boiling in the range of about 10° to about 140° F. and a high boiling fraction comprising alkyl fluorides and hydrocarbons boiling above about 140° F., and
   b. passing said low boiling fraction as said alkyl fluorides to said second stage.

8. A process according to claim 7 which further comprises the step of subjecting said high boiling fraction to dehydrofluorination conditions to form olefins and HF.

9. A process according to claim 8 wherein said olefins and HF produced upon dehydrofluorinating said high boiling fraction are recycled to said first stage as a least part of the feed.

10. A process according to claim 6 wherein said olefins and said isoparaffin comprises $C_4$ olefinic and isoparaffinic hydrocarbons.

* * * * *